(12) United States Patent
Campidelli et al.

(10) Patent No.: US 9,597,677 B2
(45) Date of Patent: Mar. 21, 2017

(54) METHOD FOR FUNCTIONALIZING CARBON NANO-OBJECTS, COMPOSITION COMPRISING FUNCTIONALIZED CARBON NANO-OBJECTS SUSPENDED IN AN ORGANIC SOLVENT AND USES THEREOF

(71) Applicant: COMMISSARIAT ÁL'ÉNERGIE ATOMIQUE ET AUX ÉNERGIES ALTERNATIVES, Paris (FR)

(72) Inventors: Stéphane Campidelli, Rambouillet (FR); Guillaume Clave, Elancourt (FR)

(73) Assignee: COMMISSARIAT ÁL'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 128 days.

(21) Appl. No.: 14/377,606

(22) PCT Filed: Feb. 13, 2013

(86) PCT No.: PCT/EP2013/052892
§ 371 (c)(1),
(2) Date: Aug. 8, 2014

(87) PCT Pub. No.: WO2013/120907
PCT Pub. Date: Aug. 22, 2013

(65) Prior Publication Data
US 2015/0298115 A1 Oct. 22, 2015

(30) Foreign Application Priority Data
Feb. 13, 2012 (FR) ...................................... 12 51331

(51) Int. Cl.
| | | |
|---|---|---|
| *A61K 9/14* | (2006.01) | |
| *B01J 37/04* | (2006.01) | |
| *B01J 13/14* | (2006.01) | |
| *A61K 49/18* | (2006.01) | |
| *B01J 31/06* | (2006.01) | |
| *B01J 31/12* | (2006.01) | |
| *B01J 35/00* | (2006.01) | |
| *B01J 37/02* | (2006.01) | |

(52) U.S. Cl.
CPC ........... *B01J 37/04* (2013.01); *A61K 49/1884* (2013.01); *B01J 13/14* (2013.01); *B01J 31/06* (2013.01); *B01J 31/123* (2013.01); *B01J 35/004* (2013.01); *B01J 37/0219* (2013.01)

(58) Field of Classification Search
CPC ....................................................... B01J 37/04
See application file for complete search history.

(56) References Cited

U.S. PATENT DOCUMENTS

| | | | |
|---|---|---|---|
| 2007/0116627 A1* | 5/2007 | Collier ................ | B82Y 10/00 423/447.2 |
| 2007/0184267 A1 | 8/2007 | Mioskowski et al. | |
| 2010/0137528 A1 | 6/2010 | Sample et al. | |
| 2011/0076497 A1 | 3/2011 | Ziegler et al. | |

FOREIGN PATENT DOCUMENTS

WO       2009095390 A2      8/2009

OTHER PUBLICATIONS

Chen, W., et al., "Coating Individual Single-Walled Carbon Nanotubes with Nylon 6,10 through Emulsion Polymerization", "Applied Materials and Interfaces", Jul. 30, 2009, pp. 1821-1826, vol. 1, No. 8.
Das, S., et al., "Localized In situ Polymerization on Graphene Surfaces for Stabilized Graphene Dispersions", "Applied Materials and Interfaces", May 3, 2011, pp. 1844-1851, vol. 3.
Lattuada, M., et al., "Functionalization of Monodisperse Magnetic Nanoparticles", "Langmuir", Dec. 29, 2006, pp. 2158-2168, vol. 23.
Roquelet, C., et al., "II-Stacking Functionalization of Carbon Nanotubes through Micelle Swelling", "ChemPhysChem", Apr. 6, 2010, pp. 1667-1672, vol. 11.
Terpetschnig, E., et al., "Synthesis of Squaraine-N-Hydroxysuccinimide Esters and Their Biological Application as Long-Wavelength Fluorescent Labels", "Analytical Biochemistry", 1994, pp. 197-204, vol. 217.
Wagner, R., et al., "Synthesis of Ethyne-Linked or Butadiyne-Linked Porphyrin Arrays Using Mild, Copper-Free, Pd-Mediated Coupling Reactions", "J. Org. Chem.", 1995, pp. 5266-5273, vol. 60.

* cited by examiner

*Primary Examiner* — Paul Dickinson
(74) *Attorney, Agent, or Firm* — Hulquist, PLLC; Mary B. Grant (57) ABSTRACT

The invention relates to a method allowing functionalization of carbon nano-objects and in particular carbon nanotubes and graphene nanosheets, a composition comprising nano-objects functionalized by this method, suspended in an organic solvent, as well as to the uses of this composition. Suitable applications include elaboration of composite materials and, in particular, of nano-composite materials, materials intended for photovoltaics, detection devices of the detector/sensor or biodetector/biosensor type, photocatalysis systems, targeted vectorization systems for compounds of therapeutic or diagnostic interest or further contrast agents for medical imaging.

19 Claims, 9 Drawing Sheets

METHOD FOR FUNCTIONALIZING CARBON NANO-OBJECTS, COMPOSITION COMPRISING FUNCTIONALIZED CARBON NANO-OBJECTS SUSPENDED IN AN ORGANIC SOLVENT AND USES THEREOF

CROSS-REFERENCE TO RELATED APPLICATIONS

This application is a U.S. national phase under the provisions of 35 U.S.C. §371 of International Patent Application No. PCT/EP13/52892 filed Feb. 13, 2013, which in turn claims priority of French Patent Application No. 1251331 filed Feb. 13, 2012. The disclosures of such international patent application and French priority patent application are hereby incorporated herein by reference in their respective entireties, for all purposes.

TECHNICAL FIELD

The invention relates to the field of functionalization of carbon nano-objects.

It relates more specifically to a method allowing functionalization of carbon nano-objects and in particular, of carbon nanotubes and graphene nanosheets.

It also relates to a composition comprising nano-objects functionalized by this method, suspended in an organic solvent, as well as to the uses of this composition.

The functionalization of carbon nano-objects as achieved according to the invention firstly gives the possibility of imparting to these nano-objects a capability of being dispersed and therefore of being individualized in organic solvents—which considerably facilitates their handling and their use—and this without altering the structure of these nano-objects and consequently the notably electric and optical properties which they naturally have.

Therefore, the invention may be used generally in all fields in which carbon nano-objects potentially have applications.

This functionalization, if desired, gives the possibility of further imparting to carbon nano-objects, properties such as for example properties of compatibility towards polymeric resins conventionally used in the making of composites (epoxy resins, vinylester resins, . . . ), properties for absorption of photons and transfer of these photons and/or for photo-induced charges, oxidation-reduction properties, catalysis properties, properties for recognizing and targeting chemical or biological molecules, properties for vectorization of chemical or biological molecules, magnetism properties, and still others.

The invention may therefore be more particularly used in the elaboration of:
  composite materials and, in particular, of nano-composite materials;
  materials intended for collecting energy from light and converting it into electricity (photovoltaics);
  detection devices of the type detectors/sensors or biodetectors/biosensors;
  catalysis or photocatalysis systems;
  systems for targeted vectorization of compounds of therapeutic interest (drugs, vaccines, etc.) or of diagnostic interest; and
  contrast agents for medical imaging, for example, magnetic resonance imaging (MRI).

STATE OF THE PRIOR ART

Carbon nano-objects and in particular carbon nanotubes (or CNTs) and graphene nanosheets rouse enormous interest in the field of research, both applied and fundamental research, because of the properties which are exceptional in many respects.

However, they have the drawback of being very difficult to disperse and individualize in organic solvents conventionally used in the chemical industry, which is a real obstacle to their use.

In order to solve this problem, functionalization of CNTs and graphene was proposed.

Two main functionalization routes were explored, i.e.:
  a so-called "covalent" functionalization, which consists of binding hydrophobic chemical groups through covalent bonds on the surface of CNTs or of graphene nanosheets; and
  a so-called "non-covalent" functionalization, which consists of adsorbing hydrophobic compounds via non-covalent interactions of the "n-stacking" type, van der Waals interactions or other ones, at the surface of the CNTs or graphene nanosheets.

Each of these routes is effective per se but unfortunately has its drawbacks.

Thus, "covalent" functionalization has the drawback of partly destroying the $sp^2$ carbon lattice of CNTs and of graphene nanosheets (each grafting site transforms an $sp^2$ carbon in to an $sp^3$ carbon) and, thereby altering the electrical and optical properties thereof, while "non-covalent" functionalization has the drawback that the interactions established between the adsorbed compounds and the CNTs or graphene nanosheets are very fragile and may therefore be destroyed during subsequent handling of the CNTs or graphene nanosheets, for example by filtration or heating.

This was what led K. J. Ziegler et al. to propose, in patent application US 2011/0076497, hereafter reference [1], a "non-covalent" functionalization method in which a polymer is formed around CNTs by polymerisation in situ.

This method consists of dispersing CNTs in an aqueous solution of a surfactant in order to obtain an aqueous suspension of CNTs, of mixing the suspension with a solution containing a first monomer insoluble in water in an organic solvent so as to obtain a nano-environment of the emulsion type around the CNTs, of introducing a second monomer, which is soluble in water, into the nano-environment so that the first and second monomers react together at the interface between the aqueous and organic portions of said nano-environment in order to form a polymer, and of possibly removing the organic solvent, the water and the surfactant by freeze-drying, filtration, washing and extraction.

Although of interest, the "non-covalent" functionalization method described in reference [1] has a certain number of drawbacks and limits.

Indeed, this method leads to CNTs which are functionalized by a polymer which is not found very close to the surface of these CNTs and which contains surfactant molecules which cannot be removed, which may have a negative role during the utilization of the properties imparted to the CNTs by this polymer.

Moreover, although it is stated in reference [1] that the polymer may be a homopolymer, the method described in this reference in reality only allows functionalization of the CNTs by copolymers since it applies two monomers which are necessarily different, one being soluble in water while the other is not soluble in water.

Moreover, the only practical example of an application of this method which reference [1] includes, related to the functionalization of CNTs with a condensation copolymer, in this case nylon 6,10, which is obtained by reaction between sebacoyl chloride (which is used in a carbon tetrachloride solution) and hexamethylene diamine (which is used in an aqueous solution).

According to reference [1], the polymer which is used for functionalizing the CNTs may be crosslinked. However, if one assumes the case of the single practical example of functionalization which is described in this reference, i.e. functionalization with nylon, this is a functionalization with a non-crosslinked polymer, for which the polymeric chains weakly interact with each other and non-covalently, which makes this functionalization fragile.

Further, functionalization of CNTs with nylon is based on the reaction between an acid chloride group and an amine group. Now, this type of reaction is accompanied by production of hydrochloric acid in the reaction medium and therefore by acidification of this medium, which may cause degradation of the molecules in solution, destabilization of the reaction medium and precipitation of the carbon nanotubes.

Further, it is known that acid chlorides react with water in order to give carboxylic acids which are not capable of reacting with amines in order to form amides. The reactivity of the acid chloride group towards water is therefore an additional limit to the use of this group as a polymerizable group.

Finally, the functionalization of CNTs with nylon molecules is not reversible in the sense that it is impossible to clear the CNTs from the nylon which surround them and recycle these CNTs if desired.

A method for functionalization with nylon, similar to the one described in reference [1], was also proposed for graphene nanosheets by Sriya Das et al. in ACS Applied Materials & Interfaces 2011, 3, 1844-1851, hereafter reference [2]. The drawbacks and limits of this method are the same as those mentioned earlier for functionalization of CNTs described in reference [1].

The inventors therefore have set the goal of providing a method for «non-covalent» functionalization of carbon nano-objects and more specifically of CNTs and of graphene nanosheets, which are without the multiple drawbacks exhibited by the "non-covalent" functionalization methods described to this day, and in particular, by the methods proposed in the aforementioned references [1] and [2].

In particular, the inventors set the goal of providing a «non-covalent» functionalization method of carbon nano-objects which clearly allows generation of a lattice formed with a crosslinked polymer around these nano-objects and this without confining surfactant molecules in this lattice, and which allows this polymer to be selected from a very wide range of possibilities (homo- and copolymers, organic and organo-inorganic polymers, etc.)

DISCUSSION OF THE INVENTION

These objects and further others one are achieved by the invention which firstly proposes a method for functionalizing carbon nano-objects by forming at least one layer of a crosslinked polymer around these nano-objects, which method comprises at least the following steps:

a) dispersing nano-objects in an aqueous solution of a surfactant to obtain a suspension in which each nano-object is surrounded by surfactant molecules, the hydrophobic portion of these molecules being oriented towards the nano-object and the hydrophilic portion of said molecules being in contact with the water of the suspension;

b) mixing the thereby obtained suspension with a solution comprising one or several organic and/or organo-inorganic monomers in an organic solvent non-miscible with water, the monomer(s) having a dichloromethane/deionized water partition coefficient at least equal to five at a temperature of 25° C. and including at least three polymerizable chemical groups, optionally protected with a protective group, this mixture being made with stirring in order to bring the solution of monomer(s) to the interface between the nano-objects and the surfactant molecules which surround these nano-objects;

c) removing the organic solvent from the mixture;

d) polymerizing and crosslinking the monomer(s) at the interface between the nano-objects and the surfactant molecules which surround these nano-objects, after deprotection of the polymerizable chemical groups if the latter are protected, to obtain the formation of a crosslinked polymer layer around the nano-objects, this layer being itself surrounded by surfactant molecules;

e) removing the surfactant molecules which surround the layer of crosslinked polymer; and f) recovering the thereby functionalized nano-objects.

Thus, according to the invention, not only one or several monomer(s) is(are) used, which each include at least three polymerizable chemical groups, which allows formation of a lattice formed with a crosslinked polymer around the nano-objects for which functionalization is desired, but further the polymerization/crosslinking reaction, which leads to formation of this lattice, is conducted at the interface between the nano-objects and the surfactant molecules which surround these nano-objects (and not at the interface between the surfactant molecules and the water of the suspension as described in the aforementioned references [1] and [2]). The polymer lattice is therefore formed as close as possible to the surface of the nano-objects and this without confining surfactant molecules.

The result of this is that the method of the invention leads to functionalized nano-objects which are extremely stable and resistant, which may be easily handled and notably purified without any risk of alteration or loss of material.

In the foregoing and in the following, by "carbon nano-objects" are meant objects consisting of carbon and which have, according to the ISO TS 80004-3: 2010 standard, one, two or three external dimensions at a nanometric scale, i.e. ranging from 1 to 100 nm. Within the scope of the invention, these are typically single- or multi-walled carbon nanotubes, or single- or multilayer nanosheets. However, these may also be carbon nanofibers or carbon nano-onions.

Moreover, by "polymer" is meant both a homopolymer which is derived from a single monomer and which is therefore formed with a single recurrent unit, and a copolymer which is derived from several (i.e. two or more than two) different monomers and which is therefore formed with several different recurrent units.

This is the reason why the organic solution used in step (b) of the method of the invention may comprise a single monomer or, on the contrary, a plurality of different monomers, depending on whether the intention is to functionalize the nano-objects with at least one layer of a crosslinked homopolymer and with at least one layer of a crosslinked copolymer.

The monomer(s) which may be used within the scope of the invention may be selected from very many organic or organo-inorganic compounds provided that these compounds meet the following two conditions:

(1) have a dichloromethane/water partition coefficient at least equal to 5 at a temperature of 25° C., in order to be able to impart to the narrow objects a capability of being dispersed and individualized in organic solvents; and (2) include at least three polymerizable chemical groups, in order to allow formation of a crosslinked polymer lattice around these nano-objects.

It is recalled that the partition coefficient, generally noted as K, of a compound between two non-miscible solvents is equal to the ratio of the molar concentrations which this compound has in the solvents, after having been added to a medium comprising both solvents in contact with each other and left free to be distributed between each other, these operations being carried out at a given temperature θ.

Within the scope of the invention, the solvents to be taken into consideration for determining the partition coefficient of a compound are dichloromethane and deionized water so that this partition coefficient corresponds to the ratio between the molar concentration which this compound has in dichloromethane and the molar concentration which the same compound has in deionized water, while the temperature θ to be taken into consideration is 25° C.

The dichloromethane/deionized water partition coefficient of a compound may notably be determined by the so-called "stirred flask" or "by stirring in a flask" method, which to this day remains one of the most reliable methods for determining the partition coefficients of a compound between two non-miscible solvents. This method consists of adding, into a flask, a known amount of the compound to a region formed by both solvents with equal portions, of stirring the flask, of letting both phases in presence decant. The concentration of the compound is then measured in each of the phases, for example by UV-visible spectroscopy. The measurements are preferably made three times and the partition coefficient is determined by calculating the average of these measurements.

Compounds which may be used as monomers in the method of the invention may notably be compounds provided with a chromophore, i.e. a group of atoms which includes one or several double bonds and which forms with the remainder of the molecule an alternation of double and single bonds. Such compounds may actually be used for imparting particular optical properties to the nano-objects, for example adsorption of photons and transfer of these photons and/or of photo-induced charges.

Thus, these may notably be compounds which comprise an azobenzene, anthraquinone, indigotin, triarylmethane group such as a triphenylmethane group, acridine, xanthene, β-carotene, quinoline, chlorin, porphyrin, phthalocyanin, naphthalocyanin, fluorescein, rhodamine, BODIPY (boredipyromethene), coumarin or cyanin group (for example, of the cyanin 3, cyanin 5 or cyanin 7 type), properly substituted in order to include at least three polymerizable chemical groups.

When this is a chlorin, porphyrin, phthalocyanin or naphthalocyanin group, this group may be in the form of a free base, in which case it is devoid of any metal atom or, on the contrary it may be metallated, i.e. coordinated to a metal cation, typically a transition metal atom such as zinc, copper, nickel, cobalt, iron, gold or platinum.

Compounds which may be used as monomers in the method of the invention may also be complexes of a transition metal, in which this metal is coordinated to several molecules of a same organic ligand (the complex is then said to be homoleptic) or with several molecules corresponding to different organic ligands (the complex is then said to be heteroleptic). Depending on the transition metal which they comprise, such complexes may in fact be used for imparting to the nano-objects, catalysis, photocatalysis, magnetism properties, etc, notably useful for applications in electrochemistry.

Thus, for example, these may be of hexapyridine, tris(2, 2'-bipyridine) or bis(2,2':6',2'-terpyridine) complexes of iron, cobalt or ruthenium, for which the pyridine, 2,2'-bipyridine or 2,2':6',2'-terpyridine molecules have been properly substituted so that these complexes may include at least three polymerizable chemical groups.

Compounds which may be used as monomers in the method of the invention may also be complexes of a rare earth (or lanthanide), in which the rare earth is coordinated to several molecules of a same organic ligand (the complex is then said to be homoleptic) or with several molecules corresponding to different organic ligands (the complex is then said to be heteroleptic), the ligand(s) may notably be compounds comprising a porphyrin or phthalocyanin group.

According to the rare earth which they comprise, such complexes may be used for imparting to the nano-objects, magnetic properties (for example, if the rare earth is terbium or holmium) or luminescence properties (for example if the rare earth is europium).

Compounds which may be used as monomers in the method of the invention may further consist in inorganic nanoparticles stabilized with an organic ligand.

These nanoparticles may notably be nanoparticles of a metal such as gold, of a metal alloy, of a semi-conductor such as germanium or tellurium, of an alloy with semi-conducting properties such as cadmium selenide CdSe or cadmium telluride CdTe, or a metal oxide such as titanium oxide $TiO_2$ or iron oxide (II,III), according to the properties (photocatalysis, magnetism, etc.) which are desired to be imparted to the nano-objects.

As for the polymerizable chemical groups, which the monomer(s) include(s), they may notably be thiol, selenol, real alkyne groups (also called terminal alkynes), cyclooctyn, azide, maleimide, diene, dienophile and/or haloacetyl groups, for example, bromo- or iodoacetyl groups.

According to the invention, the monomer(s) may include polymerizable chemical groups of a single type, in which case these polymerizable chemical groups are preferably thiol groups, selenol groups or real alkyne groups.

Alternatively, the monomer(s) may include polymerizable chemical groups of two different types, in which case these polymerizable chemical groups are, preferably, selected from the following pairs: thiol/maleimide, thiol/haloacetyl, real alkyne/azide, cyclooctyn/azide and diene/dienophile.

Within the scope of the invention, it is most particularly preferred that the polymerizable chemical groups be thiol groups or selenol groups because, during the polymerization/crosslinking of the monomer(s), these groups lead, for the first ones, to the formation of —S—S— bonds, and for the second ones, to the formation of —Se—Se— bonds, which may be subsequently described by means of an inorganic reducing agent of the hydride type (sodium borohydride, lithium aluminohydride, diisobutyl-aluminium hydride or the like) or by reaction with an excess of a thiolated compound (2-mercaptoethanol, dithiotreitol or the like) on a slightly alkaline aqueous medium.

Thus, the use of thiol or selenol groups as polymerizable chemical groups, provides the possibility of getting rid subsequently of the nano-objects having been functionalized with the method of the invention from the polymer layer which surrounds them and of recycling these nano-objects if desired.

Moreover, it is also preferred that the monomer(s) should include at least four polymerizable chemical groups and that the polymerizable chemical groups be located at the end of the spacer groups which the monomer(s) include(s), notably for avoiding steric hindrance problems. These spacer groups advantageously are typically saturated linear hydrocarbon groups which comprise from 2 to 8 carbon atoms and optionally one or several heteroatoms.

Examples of organic and organometalliclic monomers particularly suited to the application of the method of the invention are illustrated in the appended FIGS. 2, 3, 10 and 12.

Figure 1:
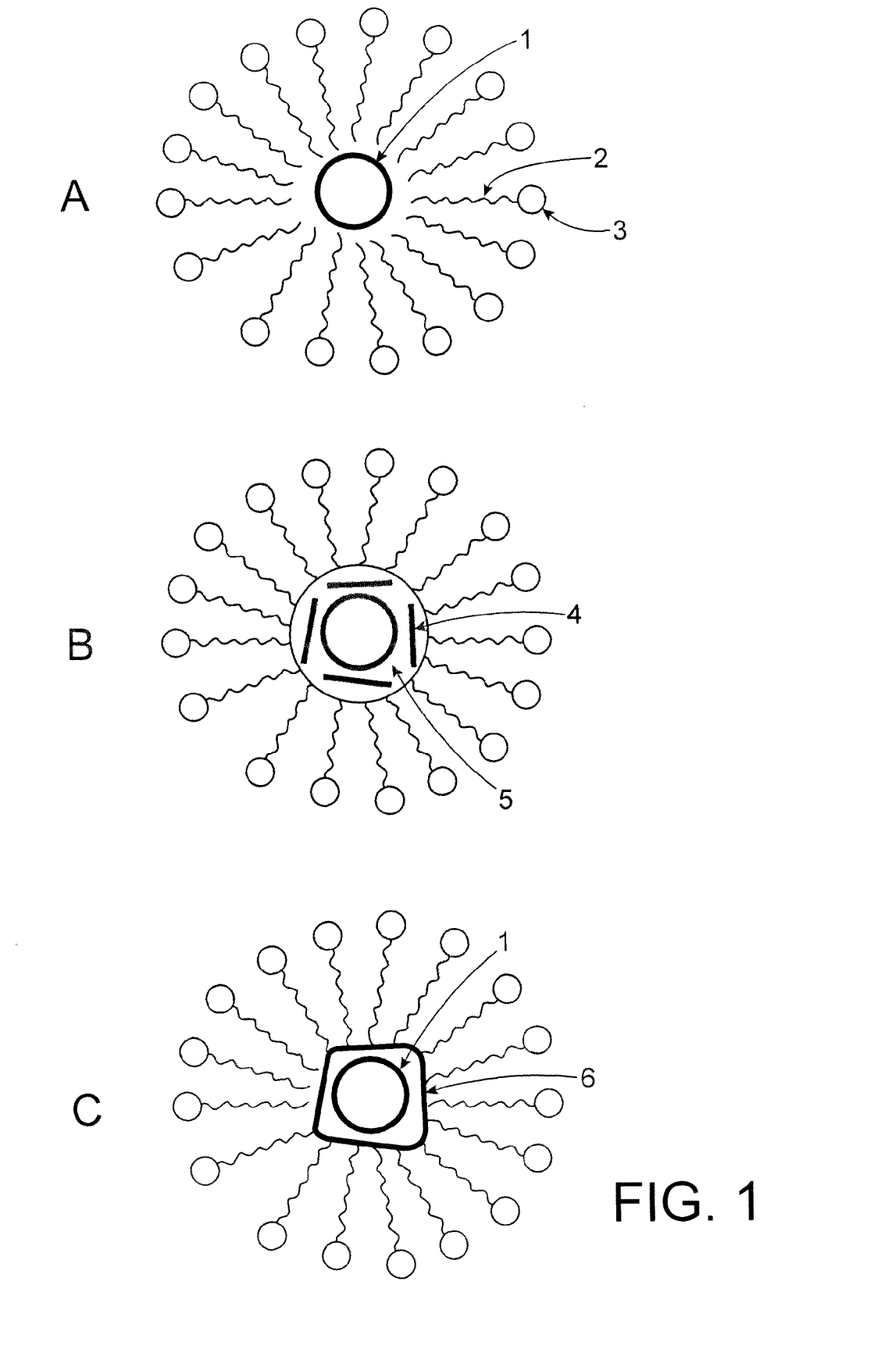
FIG. 1, already commented on, schematically illustrates, in a transverse sectional view, a carbon nano-object with a circular cross-section, for example a carbon nanotube, after:
- inclusion of this nano-object into molecules of a surfactant (part A of FIG. 1);
- penetration of a solution comprising one or several monomer(s) into an organic solvent as far as the interface between the nano-object and the surfactant molecules (part B of FIG. 1); and after
- removal of the organic solvent, deprotection of the polymerizable chemical groups of the monomer(s) if these groups are protected, and polymerization/crosslinking of the monomer(s) (part C of FIG. 1).

As mentioned earlier, the first step of the method of the invention or step a) consists of dispersing the nano-objects in an aqueous solution of a surfactant in order to obtain a suspension in which each nano-object is surrounded with surfactant molecules, the hydrophobic portion of the surfactant molecules being directed towards the nano-object and the hydrophilic portion of these molecules being in contact with the water of the suspension, as schematically illustrated on part A of the appended FIG. 1.

In this figure, reference 1 corresponds to a nano-object, seen cross-sectionally, which has been arbitrarily selected with a circular cross-section but which may have been illustrated with a different cross-section, for example, a rectangular one; reference 2 corresponds to the hydrophobic portion of the surfactant molecules surrounding the nano-object while reference 3 corresponds to the hydrophilic portion of the surfactant molecules.

According to the invention, the surfactant may be any known surfactant for allowing dispersion of carbon nano-objects in an aqueous solution. Thus, this may notably be sodium cholate, sodium dodecylsulfate, sodium 4-dodecylbenzenesulfonate, trimethyl-cetylammonium bromide, a polysorbate such as Tween™ 20, or further a surfactant which is marketed under the name of Triton X100™.

The dispersion of the nano-objects may notably be achieved by adding these nano-objects to an aqueous solution comprising the surfactant at a concentration at least equal to the critical micellar concentration (CMC) of this surfactant and preferably, at least equal to 1.2 times this CMC, and by subjecting the whole to sonication. If need be, the thereby obtained suspension may be centrifuged in order to remove the nano-objects which may have remained in the form of aggregates in spite of the sonication.

The following step, or step b), comprises the mixing of the suspension of nano-objects with a solution comprising the monomer(s) in an organic solvent non-miscible with water such as dichloromethane, chloroform or toluene, and this, with stirring in order to allow the solution of monomer(s) to penetrate between the surfactant molecules which surround the nano-objects and to reach the interface between these nano-objects and these molecules, as schematically illustrated on part B of appended FIG. 1.

In this figure, reference 4 corresponds to molecules of monomer(s) while reference 5 corresponds to the organic solvent.

The mixing of the suspension of nano-objects with the solution of monomer(s) may be achieved by adding this suspension to this solution (or vice versa) and by subjecting the whole to sonication.

It should be noted that at this stage, the monomer(s) may be present in the organic solvent in a form in which their polymerizable chemical groups are protected by a protective group, if the latter tend to react spontaneously, notably in the presence of oxygen.

Thus, for example, in the case when the monomer(s) comprise thiol or selenol groups, each of these groups is advantageously protected, for example, with an acetyl, benzoyl group or the like.

The next step, or step c) comprises the removal of the organic solvent from the mixture, which may notably be carried out by raising the temperature of this mixture while subjecting it to sonication.

In this case, the temperature to which the mixture is brought should be sufficient for allowing evaporation of the organic solvent but should nevertheless be less than the temperature from which the arrangement of the molecules or surfactant around the nano-objects risks being destroyed.

To do this, it is desirable that the mixture be brought to a temperature which does not exceed 50° C., typically from 40 to 50° C. If this temperature is insufficient for evaporating the organic solvent, taking in to account the boiling temperature of this solvent (which will for example be the case if the organic solvent is toluene), then step c) is advantageously carried out by combining the rising of the temperature with applying a vacuum to the mixture.

The next step, or step d), comprises the polymerization and the crosslinking of the monomer(s) at the interface between the nano-objects and the surfactant molecules which surround these nano-objects, in order to obtain formation of a layer of a crosslinked polymer around the nano-objects, this layer being itself surrounded by surfactant molecules as schematically illustrated in part C of the appended FIG. 1.

In this figure, reference 6 corresponds to the crosslinked polymer layer formed around the nano-object.

The conditions under which polymerization and crosslinking are achieved depend on the nature of the polymerizable chemical groups which the monomer(s) include, it being understood that it is desirable that these operations be carried out at a temperature which does not exceed 50° C. in order to avoid there also, destruction of the arrangement of the surfactant molecules around the nano-objects.

In the case when the polymerizable chemical groups of the monomer(s) are protected with a protective group, polymerization and crosslinking of the monomer(s) are preceded with deprotection of the polymerizable chemical groups.

Thus, for example, in the case when the monomer(s) include(s) thiol or selenol groups as polymerizable chemical groups and when these thiol or selenol groups are protected with an acetyl group, step d) advantageously comprises the treatment of the nano-objects obtained at the end of step c):
- with a deacetylation agent of the hydroxylamine, hydrazine or ammonia type, which is used in excess relatively to the thiol or selenol groups, in order to deprotect these groups; and then
- with a base of the triethylamine or diisopropylethylamine type, which is also used in excess relatively to the thiol or selenol groups, under an oxidizing atmosphere, for example under oxygen flow, in order to induce polymerization and crosslinking of the monomer(s) by reaction of these groups with each other.

This treatment is preferably carried out at room temperature.

If need be, it is obvious that compounds with a nature for initiating and/or accelerating polymerization and crosslinking of the monomer(s) may be used in step d).

The next step, or step e), comprises the removal of the surfactant molecules which surround the crosslinked polymer layer.

This operation may notably be carried out by filtering the suspension of nano-objects obtained at the end of step d) on a membrane resistant to organic solvents and the porosity of which allows only retention of the nano-objects, for example a membrane in polytetrafluoroethylene (Teflon™) with a porosity of 0.2 μm, and by successively rinsing the nano-objects with large volumes of water and of different organic solvents such as methanol, acetone, tetrahydrofurane, N-methylpyrrolidone, dichloromethane and diethyl ether.

The functionalized nano-objects, thus cleared of the surfactant molecules which surrounded them as well as of the reaction residues (unreacted monomer(s), excess reagents), may then be recovered and easily dispersed, optionally with ultra-sound, in an organic solvent such as N-methylpyrrolidone or N,N-dimethylformamide.

Stable suspensions of carbon nano-objects are thus obtained, which may be diluted with many organic solvents (methanol, ethanol, ethyl acetate, tetrahydrofurane, dichloromethane, chloroform, toluene, etc.) and thus kept either diluted or not for several months without any risk of precipitation.

Further, the functionalized nano-objects present in the suspensions may easily be separated from the organic solvent in which they are found, by example by filtration, and be subject to subsequent manipulations without any risk of alteration of their structure and/or of their properties.

Thus, it is notably possible to complete the functionalization of these nano-objects by forming, on the crosslinked polymer layer which surrounds them, one or several additional layers of crosslinked polymer(s), in which case the succession of steps a) to f) of this method is repeated as many times as the number of additional crosslinked polymer(s) layers, the formation of which is desired.

The method of the invention in addition to the aforementioned advantages has those:
- of providing a wide choice of functionalizations since the functionalization may be both achieved in the form of a layer or of several layers of polymer(s), these layers may be both identical with each other or different from each other, of an exclusively organic nature and as well of an organo-inorganic nature, and may both comprise a homopolymer and a copolymer;
- of being applicable to any kinds of carbon nano-objects: single-walled nanotubes of the CoMoCAT™ type as marketed by Sigma-Aldrich under references SG 65 and SG 76, nanotubes produced by laser ablation, single- or multi-walled nanotubes as marketed by Nanocyl, single-walled carbon nanotubes as marketed by Carbon Solutions, Inc., graphene nanosheets as marketed by Nanointegris under the name of Puresheets™ Mono or Quattro, etc.; and
- of only applying operations which may be carried out in an aqueous medium and under mild conditions, notably in terms of temperature, since these operations may be either carried out at room temperature or at temperatures not very far from room temperature.

An object of the invention is also a composition which comprises carbon nano-objects suspended in an organic solvent and in which the carbon nano-objects are surrounded by at least one layer of a crosslinked polymer.

As mentioned earlier, these nano-objects are typically carbon nanotubes or graphene.

Further an object of the invention is a use of this composition for making composite materials, materials intended for photovoltaics, detection devices of the detector/sensor or biodetector/biosensor types, photocatalysis systems, targeted vectorization systems for compounds of therapeutic or diagnostic interest or contrast agents for medical imaging.

Other features and advantages of the invention will become better apparent upon reading the description supplement which follows, which relates to examples for applying the method of the invention.

Of course, these examples are only given as an illustration of the object of the invention and by no means are a limitation of this object.

SHORT DESCRIPTION OF THE DRAWINGS

It should be noted that on part A of FIG. 5, the surfactant molecules, although present, have voluntarily not been illustrated for reasons of legibility.

DETAILED DISCUSSION OF PARTICULAR EMBODIMENTS

Introductory Remark:

In the examples which follow, all the sonications were carried out by using an electronic ultrasound bath Elma™, model T 490DH, with a frequency of 40 kHz and delivering at full power 130 watts with peaks ranging up to 260 watts. The sonication power may be modified with an arbitrary scale ranging from 20 to 140%. Also, in the following, mild sonication corresponds to the use of a power level ranging from 20 to 40% moderate sonication corresponds to the use of a power level ranging from 60 to 80% whilst strong sonication corresponds to the use of a power level ranging from 100 to 140%.

Example 1

Figure 2:
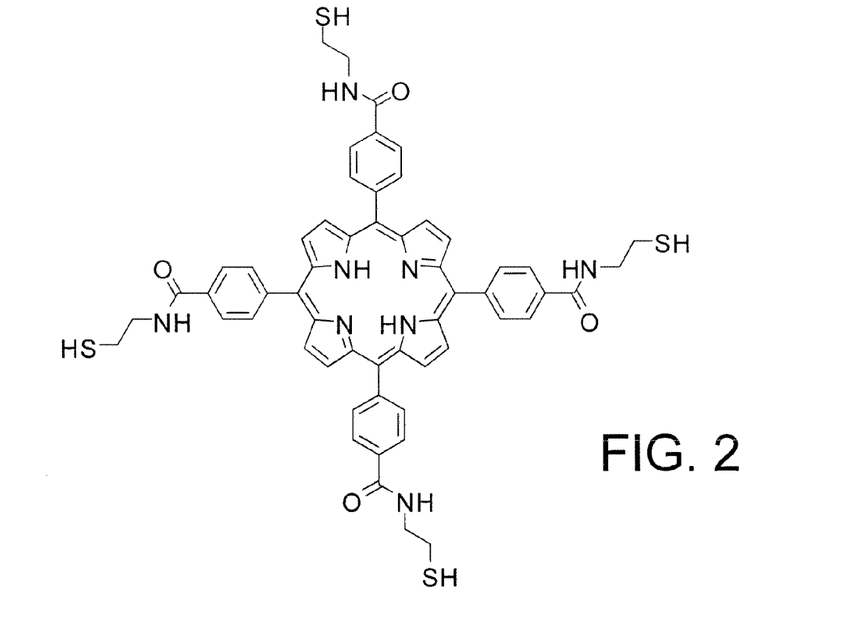
FIG. 2 illustrates a first example of a monomer which may be used in the method of the invention, which corresponds to a derivative of the free base, 5,10,15,20-tetra(4-carboxyphenyl)porphyrin, which includes four thiol groups as polymerizable chemical groups and in which each thiol group is connected to one of the carboxylic acid groups of the porphyrin via a spacer group —NH—$(CH_2)_2$—.

Functionalization of Single-Walled Carbon Nanotubes With a Layer of an Organic Polymer In this example, single-walled CNTs are functionalized with a layer of an organic polymer which is derived from the polymerization/crosslinking of a monomer of FIG. 2, designated as monomer 1 hereafter.

To do this, an aqueous suspension of CNTs is prepared on the one hand by dispersing 0.060 mg of CoMoCAT™ SG 65 CNTs (Sigma-Aldrich) into 4 ml of an aqueous solution of 2% by mass of sodium cholate and, a solution comprising 1 mg of the monomer 1 on the other hand, in a form in which each of its thiol groups is protected by an acetyl group (—CO—$CH_3$), in 600 µL of dichloromethane (DCM).

Figure 4:
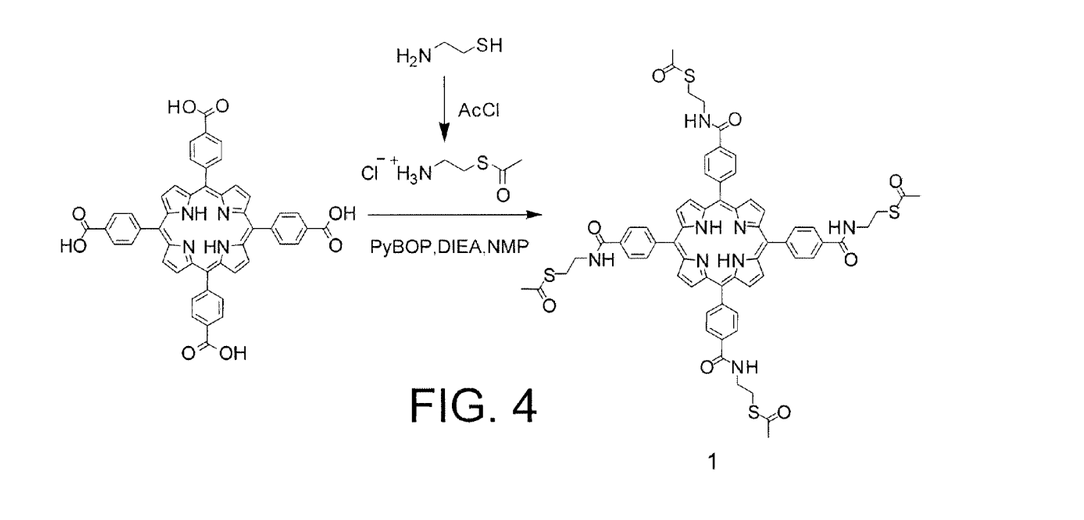
FIG. 4 illustrates a reaction scheme with which it is possible to synthesize the monomer of FIG. 2, in a form in which each of its thiol groups is protected by an acetyl group, from the free base 5,10,15,20-tetra(4-carboxyphenyl)-porphyrin.

The monomer 1, with its protected thiol groups, was obtained beforehand from the free base 5,10,15,20-tetra(4-carboxyphenyl)porphyrin, by reacting, as shown in FIG. 4, this porphyrin with S-acetylcysteamine hydrochloride in the presence of benzotriazol-1-yl-oxy-tripyrrolidinophosphonium hexafluorophosphate (PyBOP) and of N-ethyl-N,N-diisopropylamine (DIEA) in N-methyl-2-pyrrolidone (NMP), under standard conditions. The S-acetylcysteamine hydrochloride was itself obtained beforehand by reaction between cysteamine and acetyl chloride.

In order to functionalize the CNTs, the organic solution of monomer 1 is added in a reactor to the aqueous suspension of CNTs.

Both phases present in the reactor are then subject to strong sonication, with a duration of 30 minutes, in order to obtain mixing of these phases and penetration of the organic solution of monomer 1 as far as the interface between the CNTs and the sodium cholate molecules which surround them.

And then, mild sonication is carried out, with a duration of one hour, with heating to 40° C., in order to obtain evaporation of the DCM without disorganizing the sodium cholate molecules which surround the CNTs.

Figure 5:
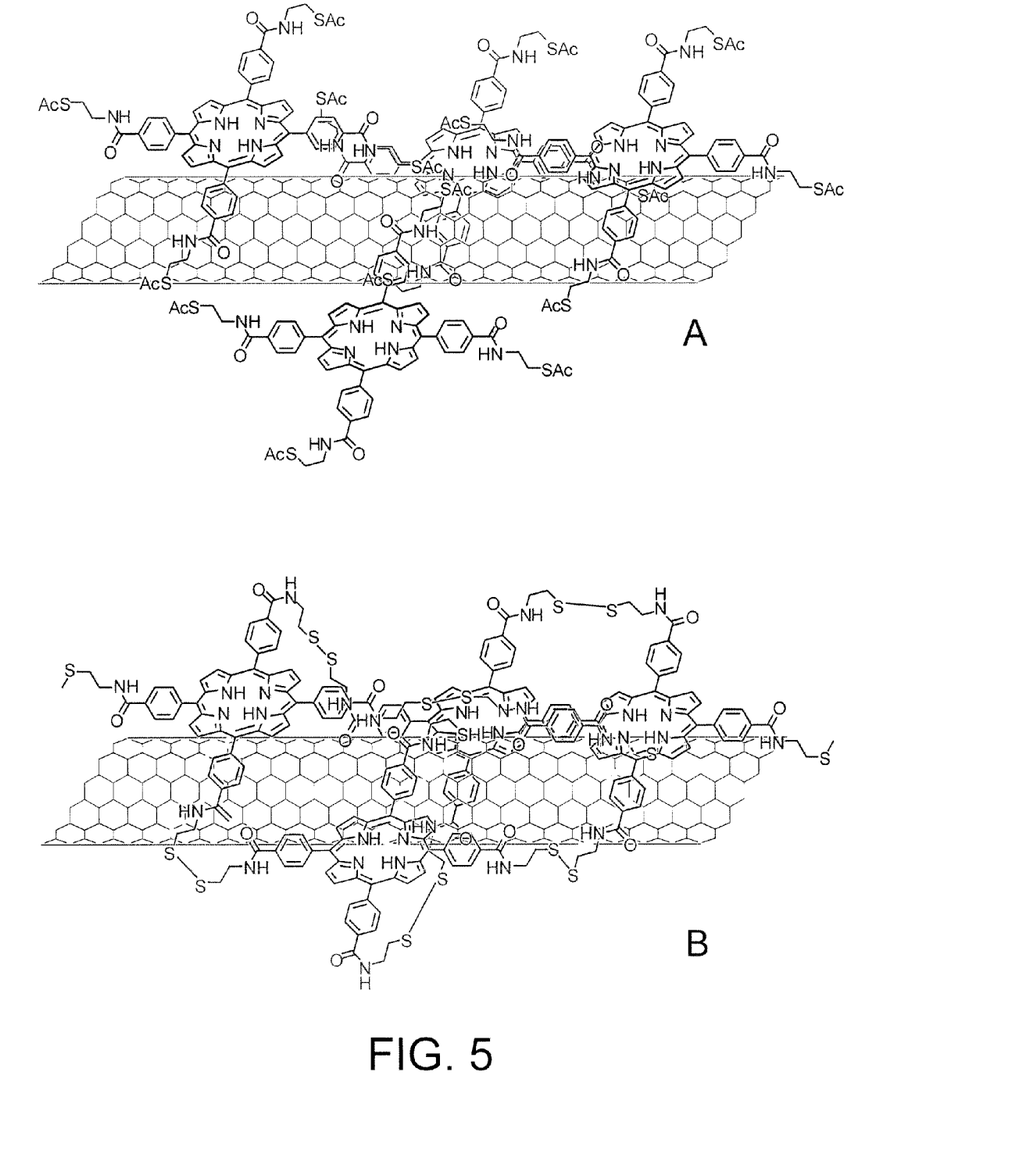
FIG. 5 schematically illustrates a single-walled carbon nanotube as obtained:
- after penetration, as far as the interface between this nanotube and the surfactant molecules which surround it, of an organic solution comprising the monomer of FIG. 2, for which each of the thiol groups is protected with an acetyl group (part A of FIG. 5); and
- after deprotection of the thiol groups of this monomer, polymerization/crosslinking of said monomer and removal of the layer of surfactant molecules (part B of FIG. 5).

An aqueous suspension of CNTs is then obtained, in which the CNTs are surrounded by a layer of monomer 1 molecules—as schematically illustrated on part A of FIG. 5—, this layer of molecules being itself surrounded by sodium cholate molecules.

An aqueous 17 M hydroxylamine solution (400 equivalents relatively to the monomer 1) is then added in to the reactor and the contents of the reactor are stirred for one hour, at room temperature, in order to deprotect the thiol groups of the monomer 1.

And then, triethylamine (400 equivalents relatively to the monomer 1) is added to the reactor and the contents of the reactor are stirred for 14 hours, under an oxygen atmosphere, in order to allow polymerization and crosslinking of the monomer 1.

After which, the contents of the reactor are filtered on a polytetrafluoroethylene (Teflon™) membrane, having pores with a diameter of 0.2 µm and the residue retained on this membrane is successively rinsed with large volumes of water, of methanol, of acetone, of NMP, of tetrahydrofuran (THF) and of DCM, in order to remove the unreacted molecules of the monomer 1, the excess reagents as well as the sodium cholate molecules surrounding the CNTs.

And then, the residue is dispersed in the 4 mL of anhydrous NMP, with moderate sonication, for 10 minutes.

A suspension of CNTs in NMP is thereby obtained, in which the CNTs are functionalized with a layer of a polymer resulting from the reaction of molecules of monomer 1 with each other and forming a shell around the CNTs, as schematically illustrated in part B of FIG. 5.

Figure 6:
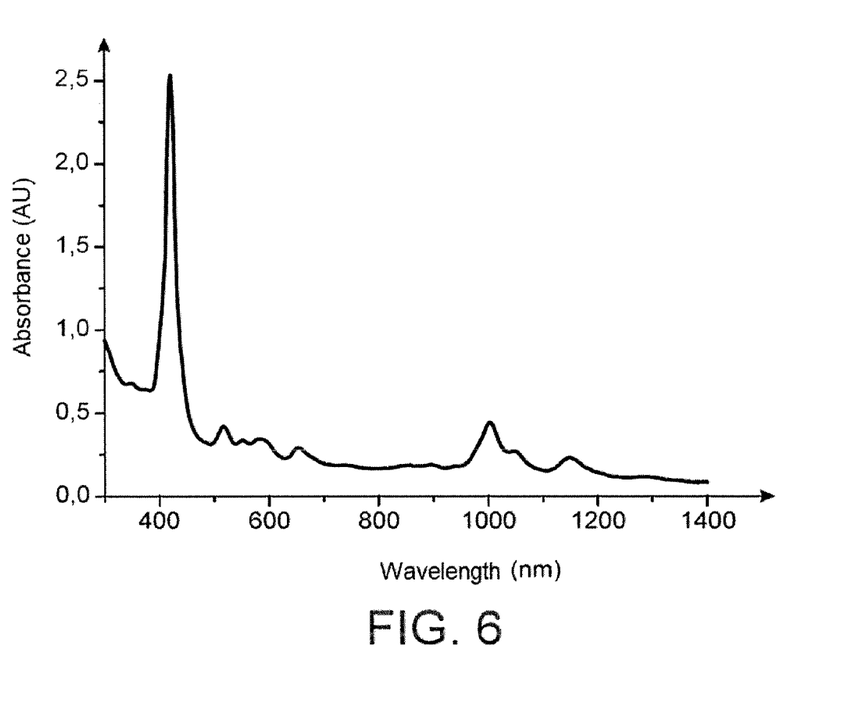
FIG. 6 illustrates the UV-Visible-NIR absorption spectrum (300-1,400 nm) of single-walled carbon nanotubes of the CoMoCAT™ SG 65 type as illustrated in FIG. 5B, suspended in N-methyl-2-pyrrolidone.

The UV-Visible-NIR absorption spectrum (300-1,400 nm) of the thereby obtained functionalized CNTs suspended in NMP (after dilution of the suspension in order to avoid a saturation of the signal emitted by the recurrent units from the monomer 1), is illustrated in FIG. 6. This spectrum has a peak at 420 nm which confirms the presence of said polymer layer around the CNTs.

Figure 7:
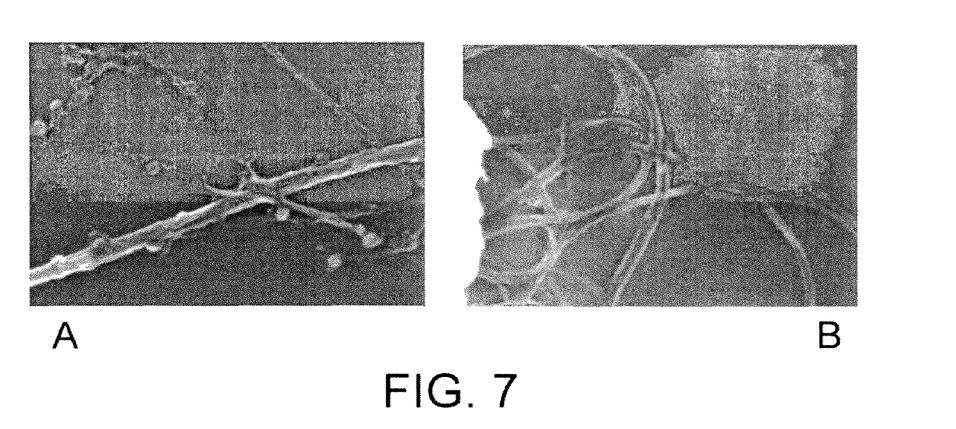
FIG. 7 corresponds to images taken with a scanning electron microscope (SEM), of single-walled carbon nanotubes, part A of this figure corresponding to carbon nanotubes as illustrated in part B of FIG. 5, and part B of FIG. 7 corresponding to carbon nanotubes not having been functionalized by the method of the invention.

Moreover, the pictures taken with the SEM of FIG. 7 show a difference between the aspect which the thereby functionalized CNTs (part A of FIG. 7) have and the one which they had before functionalization (part B of FIG. 7).

Example 2

Figure 3:
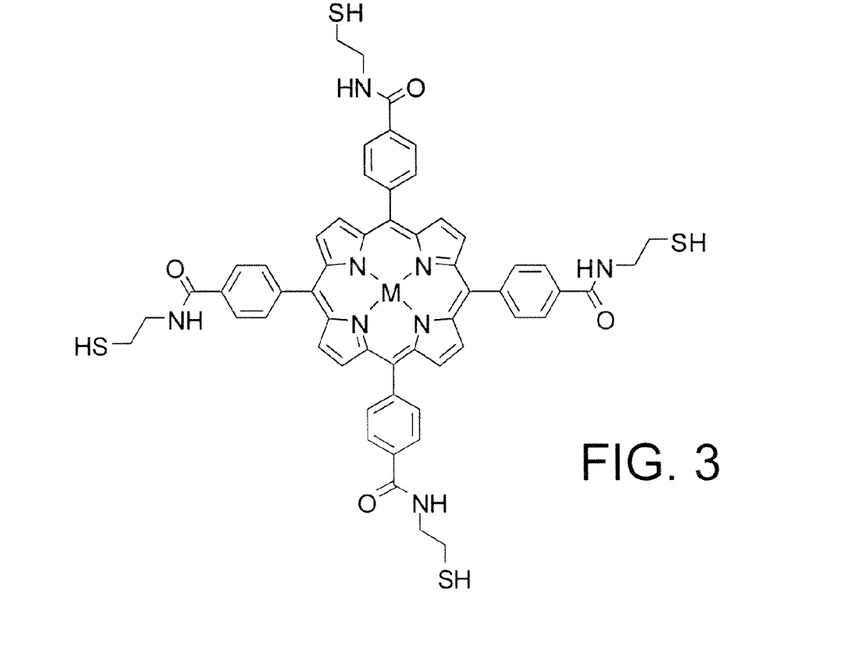
FIG. 3 illustrates a second example of monomers which may be used in the method of the invention, which correspond to derivatives of metallated 5,10,15,20-tetra(4-carboxyphenyl)porphyrins (M representing a metal atom, for example of Zn, Cu, Co, Ni, Au, Fe, Pt, etc.), which include four thiol groups as polymerizable chemical groups and in which each thiol group is bound to one of the carboxylic acid groups of porphyrin via a spacer group —NH—$(CH_2)_2$—.

Functionalization of Single-Walled Carbon Nanotubes With a Layer of an Organometallic Polymer In this example, single-walled CNTs are functionalized with a layer of an organometallic polymer, stemming from the polymerization/crosslinking of a monomer as illustrated in FIG. 3, in which M represents a platinum atom, designated as monomer 2 hereafter.

In order to do this, an aqueous suspension of CNTs is prepared by dispersing 0.12 mg of single-walled CNTs synthesized by laser ablation (Doctor Oliver Jost—Dresden University—Germany), with an average diameter of 1.3 nm, in 6 ml of a 9.84 ml/l sodium dodecylsulfate aqueous solution on the one hand and, a solution comprising 8 mg of the monomer 2, in a form in which each of its thiol groups is protected with an acetyl group, in 600 µL of DCM on the other hand.

The monomer 2, with its protected thiol groups, was synthesized beforehand from platinum 5,10,15,20-tetra(4-carboxyphenyl)porphyrin according to a reaction scheme similar to the one illustrated in FIG. 4.

In order to functionalize the CNTs, the organic solution of monomer 2 is added in a reactor to the aqueous suspension of CNTs.

And then, the same operating procedure is followed as the one described in Example 1 hereinbefore, with the exception that the filtration residue, once it is washed, is dissolved in 6 ml (instead of 4 ml) of anhydrous NMP.

Figure 8:
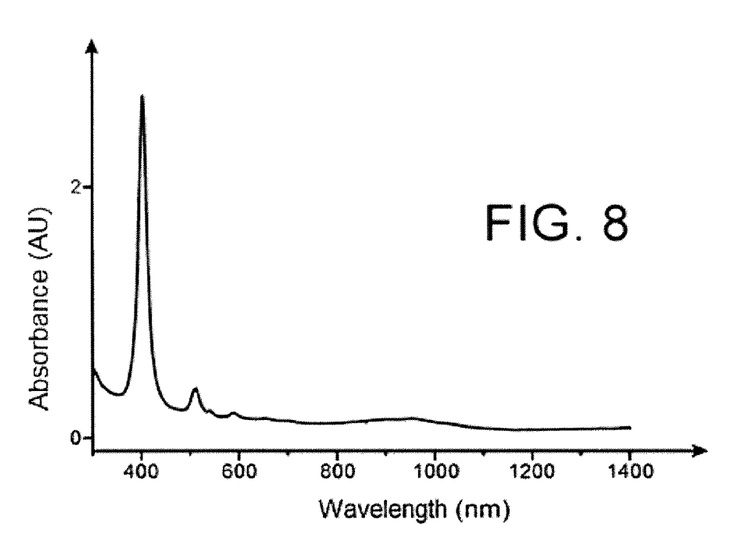
FIG. 8 illustrates the UV-Visible-NIR absorption spectrum (300-1,400 nm) of single-walled carbon nanotubes synthesized by laser ablation which were functionalized with a layer of an organometallic polymer from polymerization/crosslinking of a monomer as illustrated in FIG. 3, in which M represents a zinc atom, the carbon nanotubes being suspended in N-methyl-2-pyrrolidone.

The UV-Visible-NIR absorption spectrum (300-1,400 nm) of the thereby obtained functionalized CNTs, suspended in NMP (after dilution of the suspension in order to avoid saturation of the signal emitted by the recurrent units from the monomer 2), is illustrated in FIG. 8.

This spectrum has a peak at 400 nm which confirms the presence around the CNTs of a polymer resulting from the reaction of monomer 2 molecules with each other.

Figure 9:
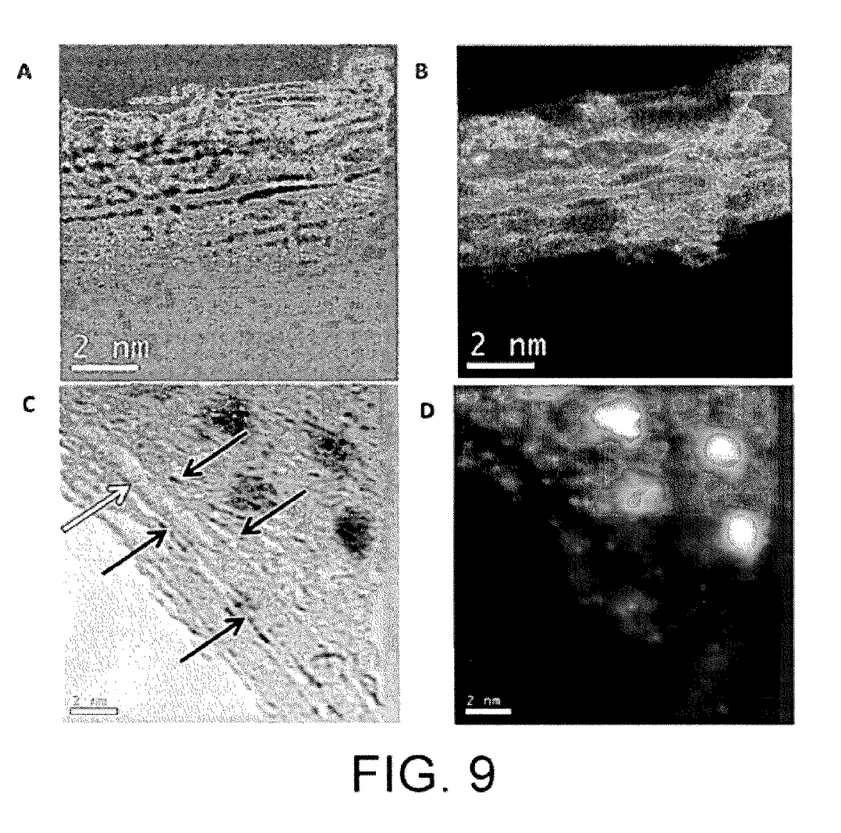
FIG. 9 corresponds to images, taken in a high resolution transmission electron microscope (TEM), of carbon nanotubes synthesized by laser ablation which were functionalized with a layer of a polymer from the polymerization/crosslinking of a monomer as illustrated in FIG. 3, in which M represents a platinum atom, part A and C of this figure corresponding to an observation of these nanotubes in a bright field mode or BF mode, and parts B and D corresponding to an observation of the same nanotubes in a high angle annular dark field (or HAADF mode).

Moreover, the pictures taken with an SEM at a high resolution of FIG. 9 show the presence at the surface of the CNTs (illustrated by the white arrow) of chains formed by recurrent units from this monomer (illustrated by black arrows).

Example 3

Figure 10:
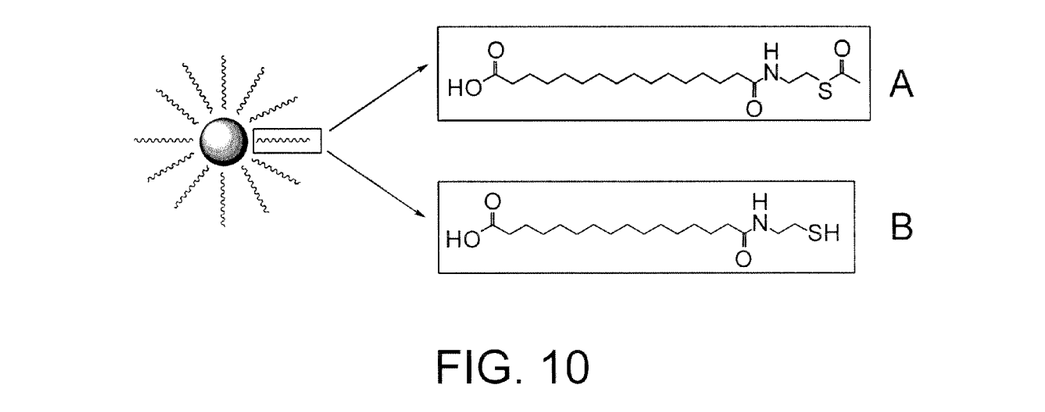
FIG. 10 illustrates a further example of monomer(s) which may be used in the method of the invention, which correspond to particles of a metal, of a semi-conductor, of an alloy with semi-conducting properties or of a metal oxide, stabilized with molecules of a ligand derived from hexadecanedioic acid, which includes a thiol group as a polymerizable chemical group and in which this thiol group is bound to one of the terminal carboxylic acid groups of the ligand via a spacer group —NH—$(CH_2)_2$—; part A of FIG. 10 shows the formula which the ligand fits when its thiol group is protected with an acetyl group, while part B of this figure shows the formula which the same ligand fits when its thiol group is not protected.

Functionalization of Single-Walled Carbon Nanotubes With a Layer of an Organometallic Polymer In this example, single-wall CNTs are functionalized with a layer of an organometallic polymer which is derived from the polymerization/crosslinking of a monomer as illustrated in FIG. 10, in which the particle is a particle of ferric oxide $Fe_3O_4$, designated as monomer 3 hereafter.

To do this, an aqueous suspension of CNTs is prepared on the one hand by dispersing 0.08 mg of CNTs synthesized by laser ablation (Doctor Oliver Jost—University of Dresden—Germany), in 4 ml of a 9.84 mmol/l sodium dodecylsulfate (SDS) solution and a solution comprising 3.5 mg of the monomer 3 is prepared on the other hand in a form in which the thiol group of each of its ligand molecules is protected with an acetyl group, in 400 µL of toluene.

The monomer 3, with its protected thiol groups, was obtained beforehand from particles of ferric oxide stabilized by oleic acid molecules (Sigma-Aldrich, reference 700312) by replacing these oleic acid molecules with molecules of the ligand shown in part A of FIG. 10, by the ligand exchange method described by Lattuada and Hatton (Langmuir 2007, 23, 2158-2168, reference [3]).

In order to functionalize the CNTs, the organic solution of monomer 3 is added in a reactor to the aqueous suspension of CNTs.

Both phases present in the reactor are then subject to strong sonication, with a duration of 30 minutes, in order to obtain the mixing of these phases and the penetration of the organic solution of monomer 3 as far as the interface between the CNTs and the SDS molecules which surround them.

Next, mild sonication is carried out with a duration of one hour with heating to 40° C., but by placing the reactor in vacuo in order to obtain evaporation of the toluene.

The same operating procedure is then followed as the one described in Example 1 hereinbefore, except that the filtration residue, once it is washed, is dispersed in 4 ml of an anhydrous NMP/toluene mixture (instead of only anhydrous NMP).

Example 4

Functionalization of Single-Walled Carbon Nanotubes With Two Layers of Polymers of Different Nature In this example, single-walled CNTs, already functionalized with a first layer of a polymer from the polymerization/crosslinking of monomer 1, are functionalized with a second layer of an organometallic polymer which itself stems from the polymerization/crosslinking of a monomer 2.

To do this, 1 ml of a suspension comprising 0.06 mg of functionalized CNTs are added in to a reactor, as obtained in Example 1 hereinbefore, in NMP, to 10 ml of a 2% sodium cholate aqueous solution.

Next, 500 µL of a solution comprising 50 µg of the monomer 2 are added in a form in which each of its thiol groups is protected with an acetyl group, in DCM, so as to obtain 2 equivalents of monomer 2 relatively to the polymer already present at the surface of the CNTs.

The same operating procedure is then followed as the one described in Example 1 herein before, except that the filtration residue, once it is washed, is dissolved in 2 ml (instead of 4 ml) of anhydrous NMP.

Figure 11:
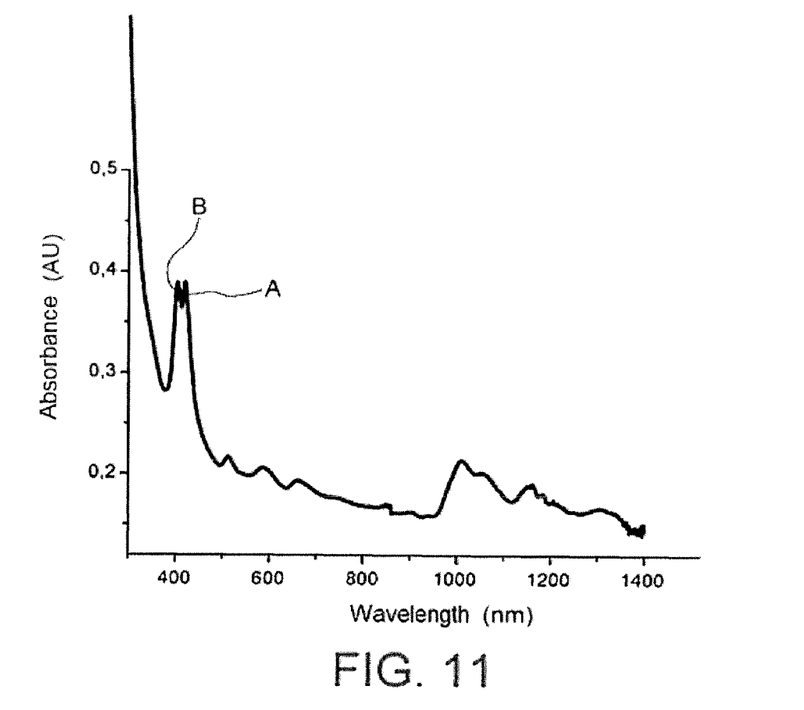
FIG. 11 illustrates the UV-Visible-NIR absorption spectrum (300-1,400 nm) of single-walled carbon nanotubes of the CoMoCAT™ SG 65 type which were functionalized with two layers of different polymers, one of which is a layer of an organic polymer from the polymerization/crosslinking of the monomer of FIG. 2, while the other one is a layer of an organometallic polymer from the polymerization/crosslinking of a monomer as illustrated in FIG. 3, in which M represents a platinum atom, the carbon nanotubes being suspended in N-methyl-2-pyrrolidone.

The UV-Visible-NIR absorption spectrum (300-1,400 nm) of the thereby obtained doubly functionalized CNTs, suspended in NMP (after dilution of the suspension in order to avoid saturation of the signals emitted by the recurrent units from the monomers 1 and 2), is illustrated in FIG. 11.

This spectrum shows the presence of two peaks: a first peak at 420 nm, noted as A, which confirms the presence around the CNTs of a first layer of a polymer resulting from polymerization/crosslinking of the monomer 1, and the second peak at 400 nm, noted as B, which confirms the presence, around the CNTs, of a second layer of a polymer resulting from the reaction of monomer 2 molecules with each other.

Example 5

Figure 12:
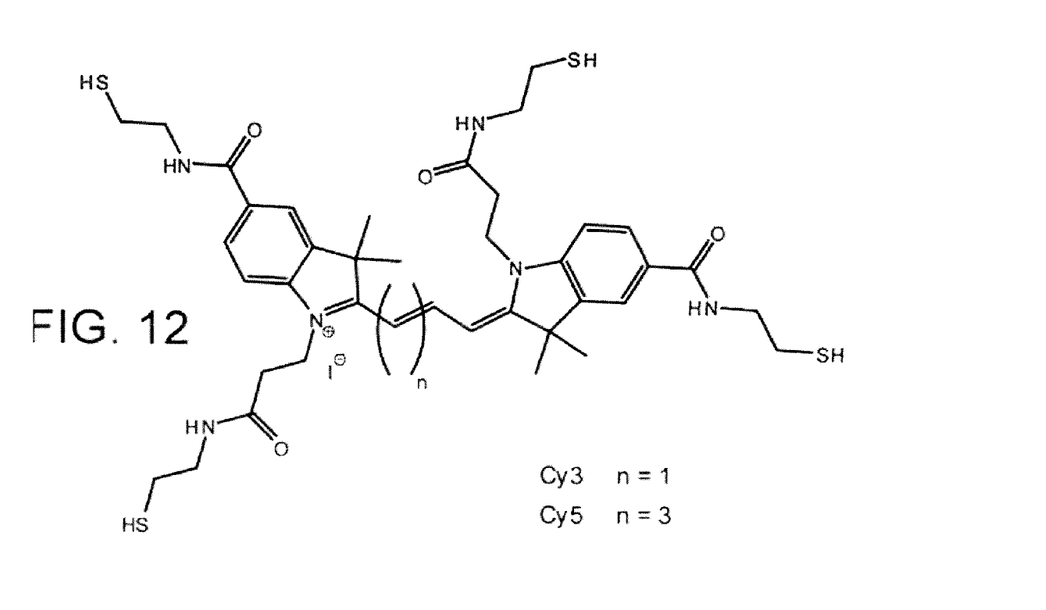
FIG. 12 illustrates a fourth example of monomers which may be used in the method of the invention, which correspond to tetracarboxylated derivatives of cyanin 3 (n=1) and of cyanin 5 (n=3), which include four thiol groups as polymerizable groups and in which each thiol group is bound to a carboxylic acid group via a spacer group —NH—$(CH_2)_2$—.

Functionalization of Single-Walled Carbon Nanotubes With a Layer of an Organometallic Copolymer In this example, single-walled CNTs are functionalized with an organometallic copolymer which stems from copolymerization/crosslinking of a monomer as illustrated in FIG. 3, in which M represents a zinc atom, monomer 4 hereafter, and of a monomer derived from cyanin 3 as illustrated in FIG. 12, monomer 5 hereafter.

To do this, an aqueous suspension comprising 0.20 mg of CNTs synthesized by laser ablation (Doctor Oliver Jost—University of Dresden—Germany) in 10 ml of a 9.84 mmol/l SDS aqueous solution on the one hand, and a solution comprising 5 mg of monomer 4 firstly in a form in which each of its thiol groups is protected with an acetyl group, and secondly 5.7 mg of the monomer 5, also in a form in which each of its thiol groups is protected with an acetyl group, in 600 µL of DCM, on the other hand.

The monomer 4, with protected thiol groups, was obtained beforehand from the monomer as illustrated in FIG. 4, by reacting this monomer with zinc diacetate (Zn(OAc)$_2$) in a medium consisting of DCM and of methanol, according to a similar procedure to the one described by Wagner et al. (J. Org. Chem. 1995, 60(16), 5266-5273, reference [4]) except that DCM was used instead of chloroform as a solvent.

Figure 13:
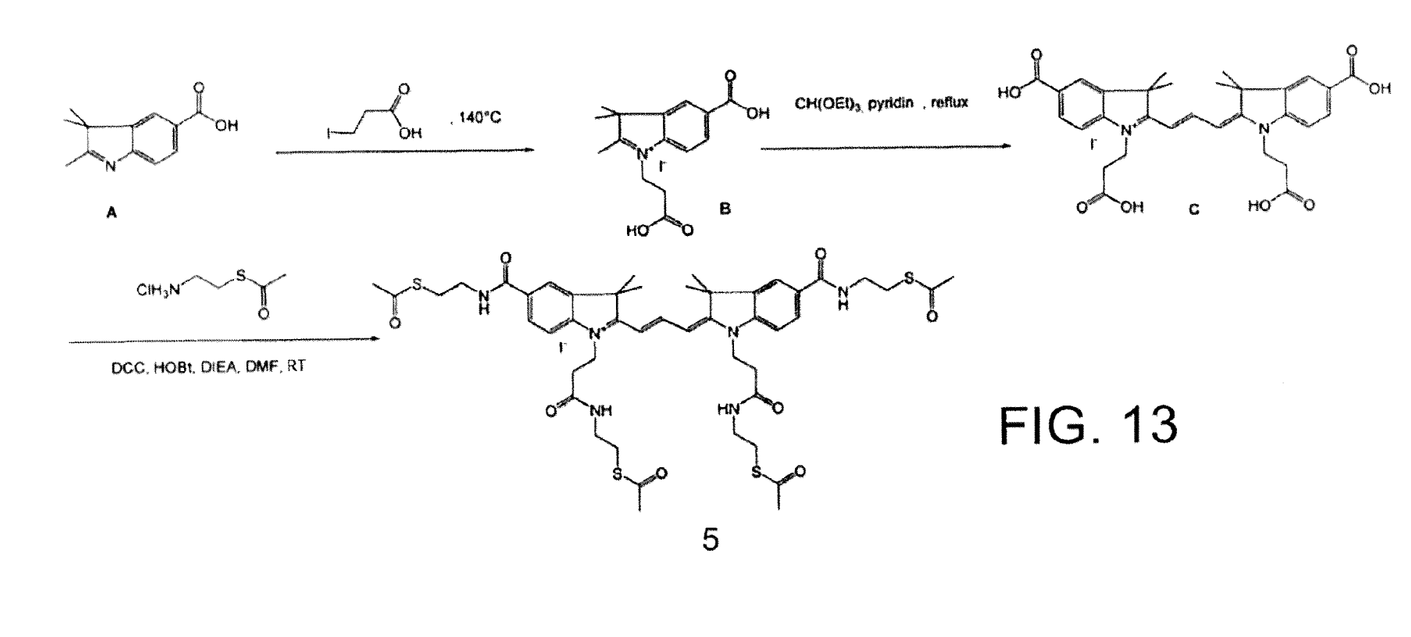
FIG. 13 illustrates a reaction scheme with which the monomer as illustrated in FIG. 12 may be synthesized, in which n=1, in a form in which each of its thiol groups is protected with an acetyl group, from 5-carboxyl-2,3,3-trimethyl-3H-indolenine.

The monomer 5, with protective thiol groups, was obtained beforehand from 5-carboxyl-2,3,3-trimethyl-3H-indolenine, by following the reaction scheme shown in FIG. 13, 5-carboxyl-2,3,3-trimethyl-3H-indolenine, noted as A in this figure, having been itself obtained beforehand by following the procedure described by Terpetschnig et al. (Analytical Biochemistry 1994, 217, 197-204, reference [5]).

In order to obtain the monomer 5, the compound A (200 mg, 1 nmol) and 3-iodopropanoic acid (1 g, 5 mmol) were introduced into a sealed tube heated to 140° C. for 4 hours. The reaction mixture contained in the compound, noted as B in FIG. 13, was cooled to 100° C. and then anhydrous pyridine (8 ml) was added. The suspension was transferred into a flask, ethyl orthoformate (40 µL, 242 µmol) was added and the suspension was heated with reflux. Two successive additions of ethyl orthoformate (40 µL, 242 µmol) separated by 2 hours are then achieved. The progression of the reaction is controlled by UV-Visible absorption with the appearance of a band at 550 nm corresponding to the compound which is noted as C in FIG. 13. The reaction is stopped when the 550 nm band stops changing.

The solvent is evaporated and the crude reaction product is dissolved in ethyl acetate (125 ml) and it is washed with a 10% by mass citric acid aqueous solution (125 ml) and then with a saturated NaCl solution (125 ml). The compound C is extracted from the organic phase with a saturated NaHCO$_3$ solution (125 ml). The phases are separated and the aqueous solution is washed with dichloromethane (125 ml) and then acidified with 1 M HCl until a pH of 2 is obtained. The suspension is extracted with ethyl acetate (200 ml), dried on anhydrous Na$_2$SO$_4$, filtered and evaporated. The compound C is obtained as a red solid.

This compound (200 mg, 291 µmol) is dissolved in anhydrous NMP, and S-acetylcysteamine hydrochloride (270 mg, 1.74 mmol), PyBOP (904 mg, 1.74 mmol) and DIEA (912 µL, 5.2 mmol) are added. The reaction medium is stirred at room temperature for 3 hours and then diluted with ethyl acetate (80 ml). The solution is washed with a 10% by mass citric acid aqueous solution (80 ml) and then with a saturated NaHCO$_3$ solution (80 ml) and then with a saturated NaCl solution (80 ml). The organic phase is dried on anhydrous Na$_2$SO$_4$, filtered and evaporated. The monomer 5 is thereby obtained.

In order to functionalize the CNTs, the organic solution of monomers 4 and 5 is added in a reactor to the aqueous suspension of CNTs.

Both phases present in the reactor are then subject to strong sonication, with a duration of 30 minutes, in order to obtain the mixing of these phases and penetration of the organic solution of monomers 4 and 5 as far as the interface between the CNTs and the SDS molecules which surround them.

And then, mild sonication is carried out, with a duration of one hour, with heating to 40° C., in order to obtain the evaporation of the DCM without destabilizing the SDS molecules which surround the CNTs.

A 28% ammonia aqueous solution (400 equivalents relatively to the monomers 4 and 5) is then added into the reactor and the contents of the reactor are stirred, for one hour at room temperature, for deprotecting the thiol groups of the monomers 4 and 5. The contents of the reactor are then stirred for 14 hours, under an oxygen atmosphere, in order to allow copolymerization and crosslinking of the monomers.

After which, the contents of the reactor are filtered on a polytetrafluoroethylene (Teflon™), membrane, having pores with a diameter of 0.2 µm and the residue retained on this membrane is successfully rinsed with large amounts of water, of methanol, of acetone, of NMP, of THF and of DCM.

And the residue is then dispersed in 6 ml of anhydrous NMP, with moderate sonication, for 10 minutes.

The UV-Visible-NIR absorption spectrum (300-1,400 nm) of the thereby obtained functionalized CNTs suspended NMP with 0.1% of TFA (after dilution of the suspension in order to avoid saturation of the signal emitted by the recurrent units from monomers 4 and 5), is illustrated in FIG. 13.

This spectrum shows the presence of two peaks, noted as A and B, respectively located at 430 nm and 570 nm, which confirms the presence around the CNTs of a copolymer resulting from a reaction of molecules of monomers 4 and 5 with each other.

Example 6

Functionalization of Graphene Nanosheets With a Layer of an Organometallic Polymer In this example, graphene nanosheets are functionalized with an organometallic polymer which stems from polymerization/crosslinking of the monomer 4.

To do this, 600 µL of a solution comprising 3 mg of the monomer 4, in a form in which each of its thiol groups is protected with an acetyl group in DCM, are added to 6 ml of an aqueous suspension which comprises 0.30 mg of a mixture of single-layer (27%), bilayer (48%), trilayer (20%), tetralayer and more (5%) graphene nanosheets, in a surfactant, and which is marketed by Nanointegris under the name of PureSheets Mono™.

The same operation procedure is then followed as the one described in Example 1 hereinbefore.

Figure 14:
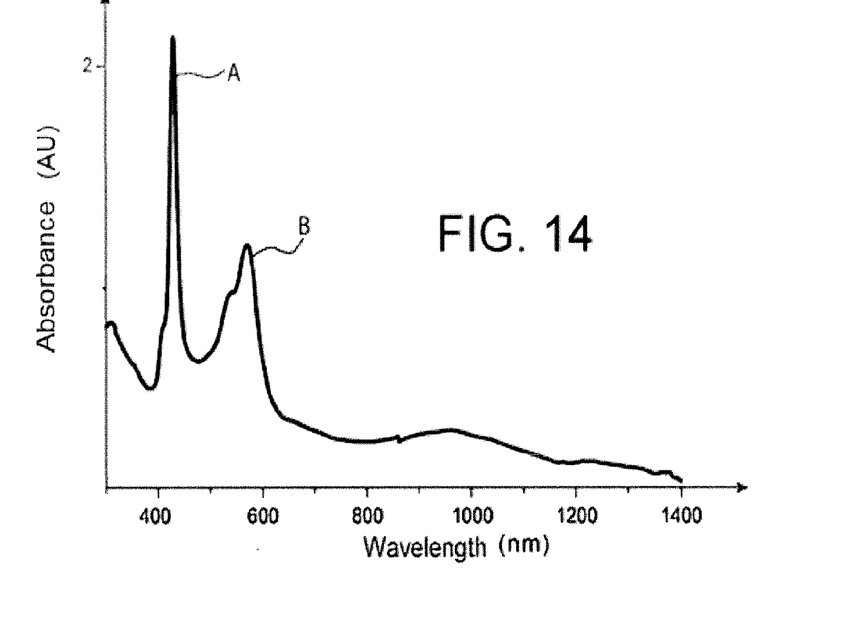
FIG. 14 illustrates the UV-Visible-NIR absorption spectrum (300-1,400 nm) of single-walled carbon nanotubes which were functionalized with a layer of an organometallic polymer from the polymerization/crosslinking of two different monomers, one of which is a monomer as illustrated in FIG. 3, in which M represents a zinc atom, while the other one is a monomer derived from cyanin 3 as illustrated in FIG. 12, the carbon nanotubes being suspended in N-methyl-2-pyrrolidone with 0.1% trifluoroacitic acid.
Figure 15:
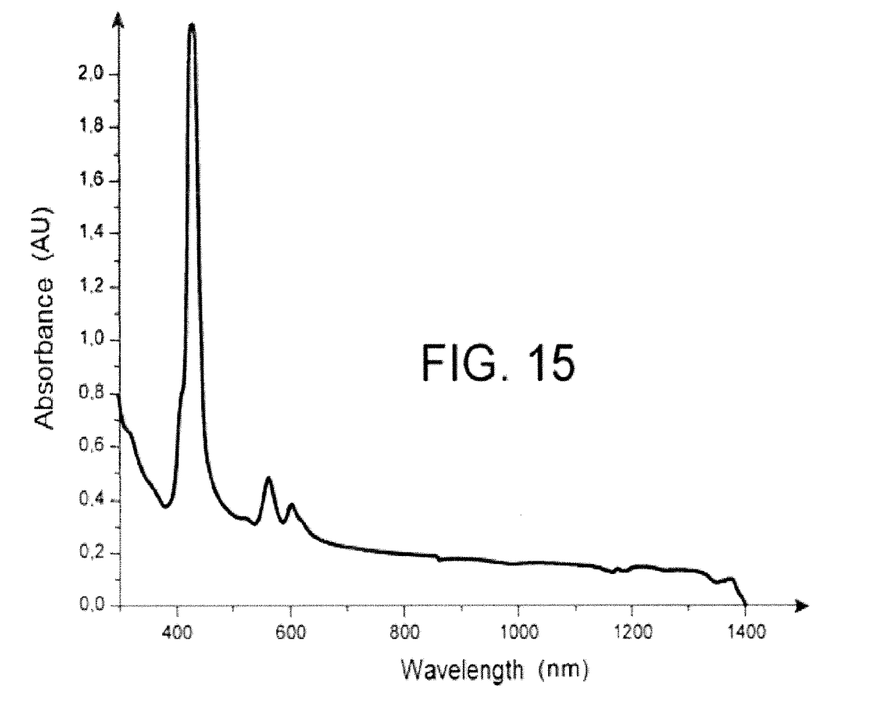
FIG. 15 illustrates the UV-Visible-NIR absorption spectrum (300-1,400 nm) of graphene nanosheets which were functionalized with a layer of an organometallic polymer from the polymerization/crosslinking of a monomer as illustrated in FIG. 3, in which M represents a zinc atom, the graphene nanosheets being suspended in N-methyl-2-pyrrolidone.

The UV-Visible-NIR absorption spectrum (300-1,400 nm) of the thereby obtained functionalized graphene nanosheets, suspended in NMP, is illustrated in FIG. 14.

This spectrum shows the presence of a peak at 420 nm which confirms the presence, around the graphene nanosheets, of a polymer resulting from a reaction of molecules of the monomer 4 with each other.

CITED REFERENCES

[1] Patent application US 2011/0076497
[2] Sriya Das et al., ACS Applied Materials & Interfaces 2011, 3, 1844-1851
[3] Lattuada et Hatton, Langmuir 2007, 23, 2158-2168
[4] Wagner et al., J. Org. Chem. 1995, 60(16), 5266-5273
[5] Terpetschnig et al., Analytical Biochemistry 1994, 217, 197-204

The invention claimed is:

1. A method for functionalizing carbon nano-objects by forming at least one layer of a crosslinked polymer around the nano-objects, comprising:
    a) dispersing the nano-objects in an aqueous solution of a surfactant to form a suspension in which each nano-object is surrounded with surfactant molecules, each surfactant molecule having a hydrophobic portion oriented towards the nano-object and a hydrophilic portion in contact with the water of the suspension;
    b) mixing the suspension formed in a) with a solution comprising at least one organic or organo-inorganic monomer in an organic solvent non-miscible with water, the monomer having a dichloromethane/deionized water partition coefficient at least equal to 5 at a temperature of 25° C. and comprising at least three polymerizable chemical groups, the mixing comprising stirring to bring the solution of the monomer to an interface between the nano-objects and the surfactant molecules surrounding the nano-objects;
    c) removing the organic solvent from the mixture obtained in b);
    d) polymerizing and crosslinking the monomer at the interface between the nano-objects and the surfactant molecules surrounding the nano-objects, to form a crosslinked polymer layer around the nano-objects, the crosslinked polymer layer being surrounded by surfactant molecules;
    e) removing the surfactant molecules which surround the crosslinked polymer layer; and
    f) recovering the thereby functionalized nano-objects.

2. The method of claim 1, wherein the nano-objects are carbon nanotubes or graphene nanosheets.

3. The method of claim 1, wherein the crosslinked polymer is a homopolymer or a copolymer.

4. The method of claim 1, wherein the monomer is selected from:
    compounds comprising a chromophore;
    complexes of a transition metal, wherein the metal is coordinated to a plurality of molecules of one or more organic ligands;
    complexes of a rare earth, wherein the rare earth is coordinated to a plurality of molecules of one or more organic ligands; and
    inorganic nanoparticles stabilized by an organic ligand.

5. The method of claim 4, wherein the monomer is selected from compounds comprising an azobenzene, anthraquinone, indigotin, triarylmethane, acridine, xanthene, β-carotene, quinoline, chlorin, porphyrin, phthalocyanin, naphthalocyanin, fluorescein, rhodamine, bore-dipyromethene, coumarin or cyanin group.

6. The method of claim 4, wherein the polymerizable chemical groups are thiol, selenol, real alkyne, cyclooctyne, azide, maleimide, diene, dienophilic and/or haloacetyl groups.

7. The method of claim 1, wherein the polymerizable chemical groups are thiol or selenol groups.

8. The method of claim 1, wherein the monomer includes at least four polymerisable chemical groups.

9. The method of claim 1, wherein the monomer comprises at least three spacer groups and the polymerizable chemical groups are located at an end of the spacer groups.

10. The method of claim 1, wherein the stirring in b) comprises a sonication.

11. The method of claim 1, wherein the sonication in c) further comprises a heating of the mixture.

12. The method of claim 11, wherein the mixture is brought to a temperature ranging from 40° C. to 50° C.

13. The method of claim 7, wherein the monomer includes thiol or selenol groups protected with an acetyl group, and d) comprises a deprotection of the thiol or selenol groups, the deprotection comprising a treatment of the nano-objects obtained in c):
    with a deacetylation agent used in excess relatively to the thiol or selenol groups, and then
    with a base used in excess relatively to the thiol or selenol groups, under an oxidizing atmosphere.

14. The method of claim 13, wherein the nano-objects are treated at room temperature.

15. The method to claim 1, wherein e) comprises a plurality of rinses of the nano-objects obtained in d) with water and then organic solvents.

16. The method of claim 1, which further comprises a dispersion of the nano-objects obtained in e) in an organic solvent.

17. The method of claim 1, wherein a) to f) are repeated at least one time.

18. The method of claim 1, wherein the polymerizable chemical groups are protected with a protective group and d) comprises a deprotection of the polymerization chemical groups.

19. A method for functionalizing carbon nano-objects by forming at least one layer of a crosslinked polymer around the nano-objects, comprising:
    a) dispersing the nano-objects in an aqueous solution of a surfactant to form a suspension in which each nano-object is surrounded with surfactant molecules, each surfactant molecule having a hydrophobic portion oriented towards the nano-object and a hydrophilic portion in contact with the water of the suspension;

b) mixing the suspension formed in a) with a solution comprising at least one organic or organo-inorganic monomer in an organic solvent non-miscible with water, the monomer having a dichloromethane/deionized water partition coefficient at least equal to 5 at a temperature of 25° C. and comprising at least three polymerizable chemical groups, the chemical groups comprising thiol or selenol groups, and the mixing comprising stirring to bring the solution of the monomer to an interface between the nano-objects and the surfactant molecules surrounding the nano-objects;

c) removing the organic solvent from the mixture obtained in b);

d) polymerizing and crosslinking the monomer at the interface between the nanoobjects and the surfactant molecules surrounding the nano-objects to form a crosslinked polymer layer around the nano-objects, the crosslinked polymer layer being surrounded by surfactant molecules;

e) removing the surfactant molecules which surround the crosslinked polymer layer; and f) recovering the thereby functionalized nano-objects.

* * * * *

UNITED STATES PATENT AND TRADEMARK OFFICE
CERTIFICATE OF CORRECTION

PATENT NO. : 9,597,677 B2  
APPLICATION NO. : 14/377606  
DATED : March 21, 2017  
INVENTOR(S) : Stephane Campidelli Page 1 of 1

It is certified that error appears in the above-identified patent and that said Letters Patent is hereby corrected as shown below:

On the Title Page

Applicant (71): "COMMISSARIAT ÀL'ÉNERGIE" should be --COMMISSARIAT À L'ÉNERGIE--.

Assignee (73): "COMMISSARIAT ÀL'ÉNERGIE" should be --COMMISSARIAT À L'ÉNERGIE--.

Attorney, Agent, or Firm (74): "Hulquist" should be --Hultquist--.

In the Specification

Column 2, Line 17: "n-stacking" should be --π-stacking--.

In the Claims

Column 18, Line 49: "method to claim 1" should be --method of claim 1--.

Signed and Sealed this  
Thirtieth Day of May, 2017

Michelle K. Lee  
*Director of the United States Patent and Trademark Office*